United States Patent [19]

Spanjers

[11] Patent Number: 5,514,968
[45] Date of Patent: May 7, 1996

[54] METHOD FOR DETECTING THE NEED FOR CALIBRATING PROBES

[75] Inventor: Henricus F. L. M. Spanjers, Ravenstein, Netherlands

[73] Assignee: Ecotechniek B.V., Utrecht, Netherlands

[21] Appl. No.: 295,907

[22] PCT Filed: Mar. 11, 1992

[86] PCT No.: PCT/NL92/00047

§ 371 Date: Nov. 14, 1994

§ 102(e) Date: Nov. 14, 1994

[87] PCT Pub. No.: WO93/18394

PCT Pub. Date: Sep. 16, 1993

[51] Int. Cl.[6] .................................................. G01N 27/00
[52] U.S. Cl. ............... 205/782.5; 324/71.2; 324/500; 324/601; 204/415; 73/1 G; 205/778.5; 205/781
[58] Field of Search ............................ 324/500, 535, 324/601, 71.2; 73/1 R, 1 G; 204/153.1, 153.17, 401, 415

[56] References Cited

U.S. PATENT DOCUMENTS

| | | | |
|---|---|---|---|
| 4,223,549 | 9/1980 | Kitzinger | 204/401 X |
| 4,457,808 | 7/1984 | Taylor et al. | 204/153.1 |
| 4,900,422 | 2/1990 | Bryan et al. | 204/401 |
| 4,921,582 | 5/1990 | Wang et al. | 204/153.1 |
| 5,376,244 | 12/1994 | Preidel | 204/153.17 X |

FOREIGN PATENT DOCUMENTS 2498761  7/1982  France .

*Primary Examiner*—Kenneth A. Wieder
*Assistant Examiner*—Diep Do
*Attorney, Agent, or Firm*—Young & Thompson

[57] ABSTRACT

An in situ probe failure detection method for probes which deliver an electric signal on account of a change of the concentration of a substance to be measured. An example of such a probe failure may be caused by, for example, fouling of the membrane as the relative change in signal may be interpreted as a change in the concentration of the substance to be measured. More particularly, the method involves detecting the need for calibrating probes, which probes deliver an electric signal on account of a change of the concentration of a substance to be measured, characterized by: (a) subjecting the probe to a stepwise change of the concentration of the substance to be measured; (b) calculating the value of the probe response time constant $t_c$ of the obtained measurement curve with the help of the following main equation (1): $t_c dy/dt = -y + \alpha_0 + \alpha_1 t$ wherein $t$=time (time), $t_c$=probe response time constant (time), $y$=substrate probe signal (mass volume$^{-1}$), $\alpha_0$=substrate concentration at start of response (mass volume$^{-1}$), $\alpha_1$=rate of change of substrate concentration (mass volume$^{-1}$ time$^{-1}$), and (c) comparing the calculated $t_c$ values of at least two different measurements with each other, and in case the calculated $t_c$ values do not match, calibrating the probe.

6 Claims, 8 Drawing Sheets

METHOD FOR DETECTING THE NEED FOR CALIBRATING PROBES

The invention relates to a method for detecting the need for calibrating probes which probes deliver an electric signal on account of a change of the concentration of a substance to be measured.

BACKGROUND OF THE INVENTION

A general problem with probes as indicated above, for instance, dissolved oxygen measuring probes (DO probes) is that probe failure caused by, for example, fouling of the membrane may be interpreted as a change in the concentration of the substance to be measured.

Normally this problem is solved by calibrating the probe on a regular time basis. However this solution is not without problems, because by periodically calibrating the probe, the calibration can be either too late or too early. When the calibration is done too early it costs too much working-hours and if the calibration is too late the probe had produced false values during an unknown period.

SUMMARY OF THE INVENTION

The above-indicated problem has been solved with the invention presented below. It has been found that the probe response time constant can be calculated periodically and that this parameter can be used for probe diagnosis.

The method is based on the fact that the response of the probe after an instant change in concentration can be modelled as a first order model combined with a ramp function:

$$t_c \frac{dy}{dt} = -y + \alpha_0 + \alpha_1 t$$

wherein t=time (time), $t_c$=probe response time constant (time), y=substrate probe signal (mass volume$^{-1}$), $\alpha_0$= substrate concentration at start of response (mass volume$^{-1}$), $\alpha_1$=rate of change of substrate concentration (mass volume$^{-1}$ time$^{-1}$). The measured response of the probe is used to calculate the constants in this equation. The probe response time constant ($t_c$) from this model can be used for probe diagnosis. As long as the probe response time does not change in consecutive measurements of the probe response after an instant change in concentration the probe is accurate. As soon as the probe response time is changed during consecutive measurements the probe should be recalibrated. In the method according to the invention the concentration of the substance to be measured is changed periodically and each time after such a change the probe response time constant is calculated. As long as the probe response time constant doesn't vary there is no problem. As soon however as the probe response time constant changes there is a probe failure and the probe has to be cleaned and calibrated. By using the method according to the invention described a new calibration is always done in time.

To prove the method, Applicant has carried out research with a continuous flow-through respiration meter (EP-B-257057). The continuous flow-through meter measures the dissolved oxygen (DO) concentration at the inlet and at the outlet of a closed respiration chamber through which the sludge is pumped continuously [Spanjets H. and Klapwijk A., (1990). On-line meter for respiration rate and short-term biochemical oxygen demand in the control of the activated sludge process. Advances in Water Pollution Control, Proceedings of the 5th IAWPRC Workshop held in Yokohama and Kyoto, Japan, 26 Jul.–3 Aug. 1990]. The respiration rate is calculated from the difference of the two DO measurements.

The electrochemical oxygen sensor used in the continuous flow-through respiration meter is based upon the electrochemical reduction of oxygen in an amperemetric cell. The electrodes are immersed in an electrolytic solution which is separated from the bulk solution by a semi-permeable membrane. The electrode signal is determined by the diffusion of dissolved oxygen (DO) from the bulk through the membrane. The probe-meter combination will be referred to as "DO-probe".

The respiration meter as described by Spanjets and Klapwijk (1987): Measurement of the toxicity of KCN and some organic compounds for the activated sludge using the Wazu-respiration meter; In: Kolaczkowski S. T. and Crittenden B. D. (eds.) Management of hazaradous and toxic wastes in the process industries; Elsevier, and Spanjars and Klapwijk (1990) loc.cit., has proven its usefulness and its reliability. The characteristic of this meter is that the DO concentration in the inlet and outlet is measured with one single probe, fixed at one opening of the chamber, by alternating the flow direction through the chamber (FIG. 1).

When the DO probe is replaced by another probe or sensor, such as a nitrate or a chlorine probe, the method according to the invention is also applicable to this kind of probes or sensors.

An aspect of this principle is that, for instance, a steady state DO reading is only available when the DO probe signal, after changing the flow direction, has reached its end value. Hence the maximum measuring frequency for the DO concentration is limited by the response time of the DO probe. Till now, in practice, the measurement of the DO takes place when the signal has reached about 95% of its ultimate value. The time needed to attain this 95% response (response measuring period) is based on experience. As both the inlet- and outlet concentration may be off the real value, a systematic error of about 10%, may occur in the calculated respiration rate. Furthermore s dirty or fouled membrane and consequently s slower DO response may result in even s higher error contribution.

As elucidated below s method is proposed to estimate the steady state DO concentration from the probe response curve, even though the full response has not yet been attained.

Furthermore the first order probe response time constant will be estimated after each response, which can be used for probe performance diagnosis. The method according to the invention is based on a least squares fit to a first order probe response model. Simulations and batch experiments are used to demonstrate the effectiveness of the method.

MODEL OF THE DO-PROBE RESPONSE

As indicated above in is assumed that the DO probe signal can be modelled by a first order dynamic system. Additionally, it is assumed that the change of the real DO concentration during the response measuring period will change along a linear slope. The response of the DO probe after a change in the flow direction can then be considered as a combined step and ramp response of a first-order system (FIG. 2).

In accordance with the invention the probe signal, for instance the DO probe signal y is modelled by a first order dynamic system:

$$t_c \frac{dy}{dt} = -y + c \quad (1)$$

Where the input c is the real DO concentration which is assumed to be a ramp function with offset $\alpha_0$ and slope $\alpha_1$:

$$c = \alpha_0 + \alpha_1 t \quad (2)$$

Combining (1) and (2) gives the response function:

$$t_c \frac{dy}{dt} = -y + \alpha_0 + \alpha_1 t \quad (3)$$

There is an analytical solution of (3) that can be written in the form:

$$y(t) = e^{-\frac{t}{t_c}} y(0) + \int_0^t e^{-\frac{(t-\tau)}{t_c}} u(\tau) d\tau \quad (4)$$

where: y(0)=the initial condition of the probe signal at time t=0.

$$u = (\alpha_0 + \alpha_1 t)/t_c$$

Inserting the value of u gives the DO response as a function of time:

$$y(t) = [(y(0) - \alpha_0 + \alpha_1 t_c) e^{-t/t_c}] + [\alpha_0 + \alpha_1 t] - [\alpha_1 t_c] \quad (5)$$

It is recognized that the first term of (5) converges to 0 after some time, determined by the probe response time. The last term of (5) is then seen to show the lag between the real DO concentration and the probe response after the transient. FIG. 3 shows the result of a simulation using (5) for different realistic values of the parameters. The simulation demonstrates that, when the real DO concentration changes along a linear slope, the ultimate value of the DO signal (y) always deviates $\alpha_1 t_c$ from the real DO concentration (c).

ESTIMATION OF DO CONCENTRATION AND PROBE RESPONSE TIME

All the three parameters $t_c$, $\alpha_0$ and $\alpha_1$ in equation (3) are unknown and have to be estimated from the DO probe step response. Since the DO measurements are obtained in time discrete form it is natural to approximate the time derivative in (3) with finite differences. Here Applicant has chosen the trapezoidal rule for integration:

$$t_c \frac{y_{k+1} - y_k}{h} = \frac{1}{2}(-y_{k+1} - y_k + \alpha_0 + \alpha_1 kh + \alpha_0 + \alpha_1(k+1)h) \quad (6)$$

where: k=1, 2, ..., K; K typically 10 or 15 h=sampling interval DO concentration, typically 1 or 2 s.

The parameter $\alpha_1$ can be estimated separately. Here Applicant has considered the last DO measurement of two consecutive step responses, called $y_K(m-1)$ and $y_K(m)$. The DO concentration slope is then estimated from:

$$\alpha_1 \approx \frac{y_K(m) - y_K(m-1)}{2Kh} \quad (7)$$

Now there remain two parameters, $t_c$ and $\alpha_0$, to be estimated. If equation (1) is applied to all K measurements (but the first) in one step response the following equations are obtained:

$$t_c(y_2 - y_1) - h\alpha_0 = \frac{1}{2}h(-y_2 - y_1 + 3h\alpha_1)$$

$$t_c(y_3 - y_2) - h\alpha_0 = \frac{1}{2}h(-y_3 - y_2 + 5h\alpha_1)$$

$$t_c(y_k - y_{k-1}) - h\alpha_0 = \frac{1}{2}h(-y_k - y_{k-1}) + (2k-1)\alpha_1) \quad (8)$$

This can be written in a vector form:

$$\begin{bmatrix} y_2 - y_1 & -h \\ y_3 - y_2 & -h \\ \vdots & \vdots \\ y_k - y_{k-1} & -h \end{bmatrix} \begin{bmatrix} t_c \\ \alpha_0 \end{bmatrix} = \begin{bmatrix} \frac{1}{2} h(-y_2 - y_1 + 3h\alpha_1) \\ \frac{1}{2} h(-y_3 - y_2 + 5h\alpha_1) \\ \vdots \\ \frac{1}{2} h(-y_k - y_{k-1} + (2k-1)h\alpha_1) \end{bmatrix} \quad (9)$$

or written in a more compact form:

$$\phi\theta = y \quad (10)$$

The unknown parameter vector $\theta$ can be estimated by the least-squares method (Åström K. J. and Wittenmark B., (1984) Computer Controlled Systems, Theory and Design, Prencetise-Hall, Inc., New York):

$$\theta = (\phi^T\phi)^{-1}\phi^T y \quad (11)$$

The estimate $\theta$ makes it possible to calculate the DO concentration at the end of the sampling interval:

$$c(m) = \hat{\alpha}_0 + \hat{\alpha}_1 Kh \quad (12)$$

This is used for a new estimate of $\alpha_1$:

$$\alpha_1 \approx \frac{(c(m) - c(m-1))}{2Kh} \quad (13)$$

c(m−1) is the calculated real DO from the foregoing response. Then a new vector $\theta$ is calculated from the observations y. This procedure is repeated until a preset error criterion is met.

This method was tested by means of two simulations and an experiment. The application of the method was demonstrated in another experiment where the probe membrane was fouled intentionally.

MATERIALS AND METHODS

In the simulations, executed with SIMON [Elmqvist H. et al., (1986) Simnon, User's guide for MS-DOS computers, SSPA Systems, Sweden], measuring data were generated with the use of the first order model (5) and chosen values of c and $t_c$. Then the method proposed was used to recalculate c and $t_c$. Any deviation of the result from the original c and $t_c$ emanates from the assumption that the time derivative of (3) can be approximated by the trapezoidal integration method.

In the laboratory experiments a respiration meter RA1000, Manorharm, equipped with a WTW dissolved oxygen meter (modified model OXY-219/R with sensor model E090), was connected to an aerator, the total system having a content of 1.5 liter of activated sludge. The sludge was sampled from a nitrifying activated sludge plant. The respiration meter which works according to the principle described by Spanjars and Klapwijk (1990 loc.cit.) was operated in a mode such that the alternating DO signal could be sampled. Temperature and pH were kept constant at 20° C. and 7.5 respectively.

In Example 1 the assumption of the first order model was tested. Therefore a known amount of ammonium was added to the sludge and the DO signal was recorded. The DO concentration at the inlet and at the outlet were either calculated from 2–4 values at the end of the response measuring period (averaging method) or calculated according to the method of the invention (estimation method). From the DO concentrations, the respiration rate and the mass of oxygen used by the nitrifiers for the oxidation of the unit of mass nitrogen (O/N ratio) were calculated respectively. The O/N ratio was compared for different situations.

In Example 2 the procedure to detect probe failure from an increasing $t_c$ was tested. Probe fouling was imitated by covering a part of the probe membrane with ball-bearing grease. Ammonium was added to the sludge before and after contamination the membrane. The effect on $t_c$ and on the O/N ratio was studied.

The invention is illustrated by means of the following examples 1 and 2.

EXAMPLE 1

Verification of the method

Test 1: Linear change of the real DO concentration (simulation)

Figure 1:
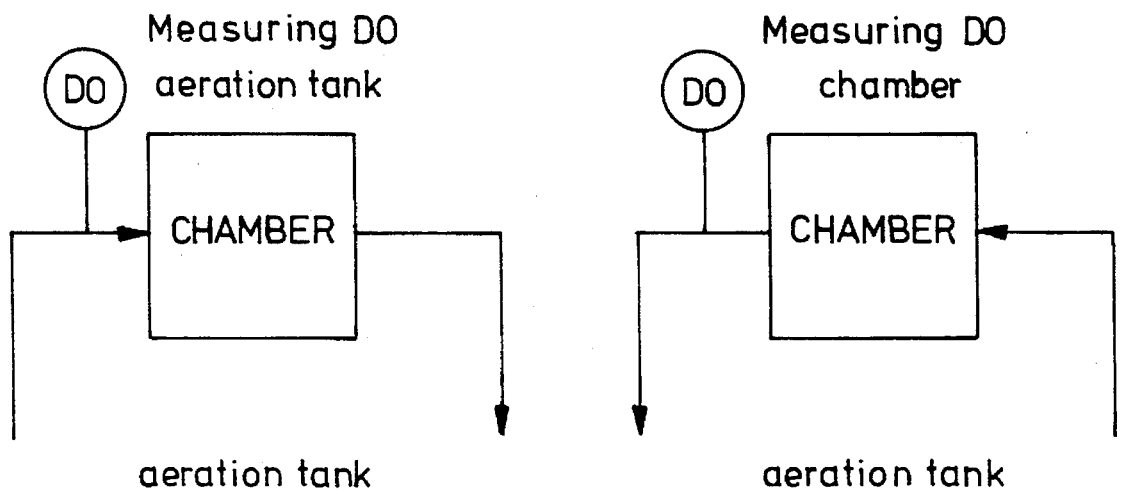
FIG. 1: Scheme of the one-probe continuous respiration meter.
Figure 2:
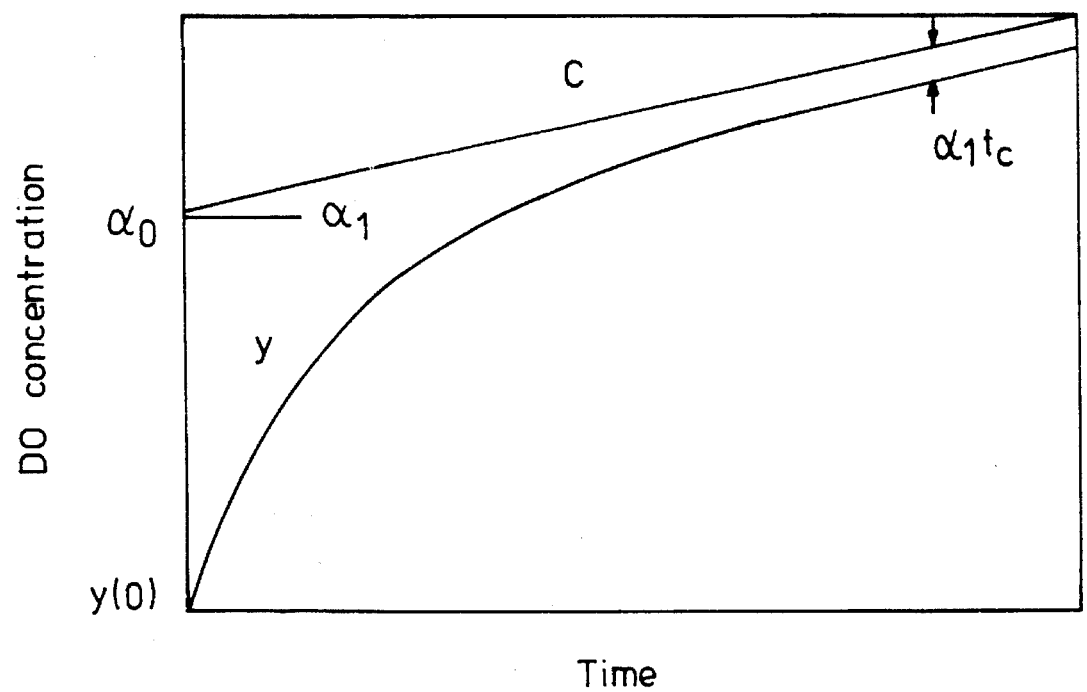
FIG. 2: Combined step and ramp response of the DO probe after changing the direction of the sludge flow. First-order linear system assumed.
Figure 3:
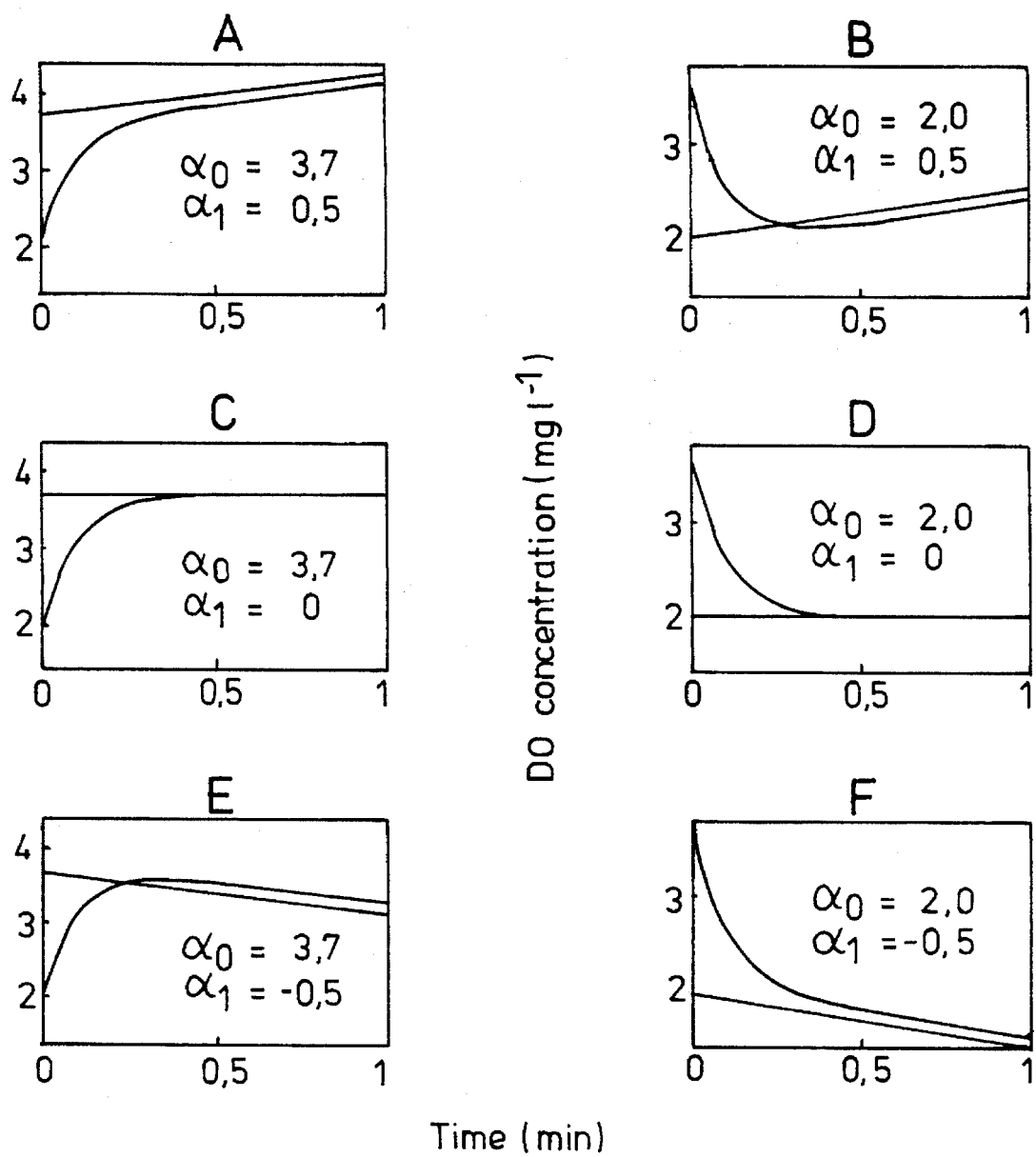
FIG. 3: Simulation, using equation (5), of the measured DO (y) after reversing the sludge flow direction i.e. after a step change in the DO (c) followed by a time linear change of c. Probe time response constant $t_c=0.10$ min.
Figure 4:
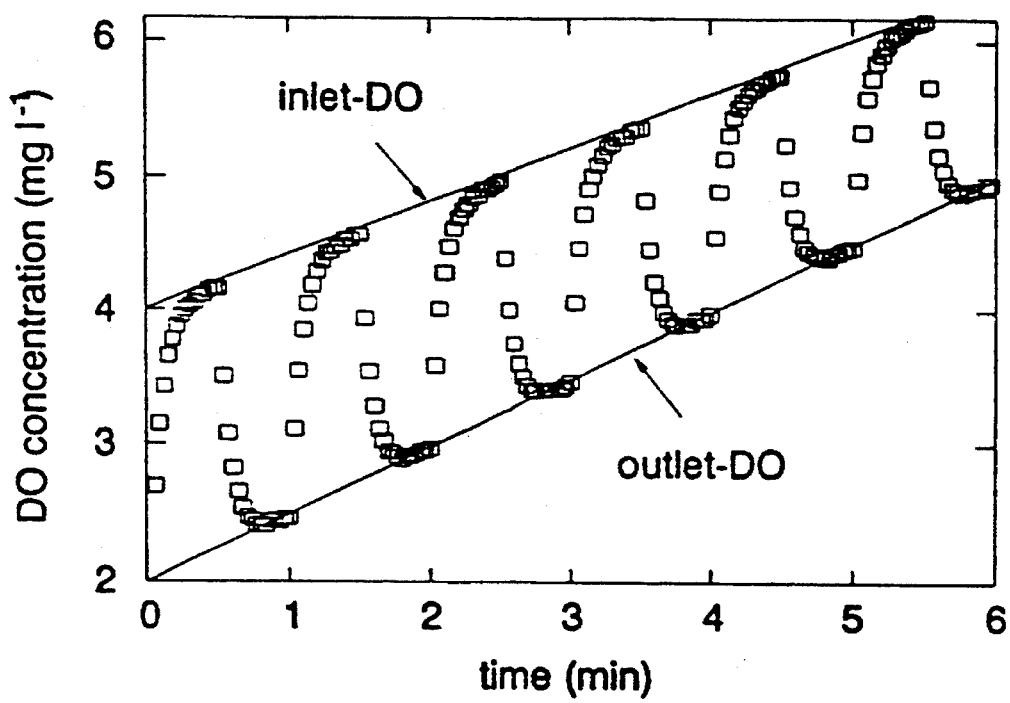
FIG. 4: Simulation, using (5), of the measured DO concentration (points) during the operation of the respiration meter in comparison to the inlet and outlet-DO (solid lines). $h=2$ s, $t_c=0.08$ min, $t_r=0.5$ min, $\alpha_0 32$ 4 g m$^{-3}$ and 2 g m$^{-3}$ for respectively the inlet and the outlet, $\alpha_1=0.4$ g m$^{-3}$ min$^{-1}$ and 0.5 g m$^{-3}$ min$^{-1}$ for respectively the inlet and the outlet. Standard deviation noise: 0.008 g m$^{-3}$.

For given constant values of $\alpha_1$, h and $t_c$, and an initial value of $\alpha_0$, equation (5) was used to simulate the course of the measured DO during a short period of respiration measurement (FIG. 4). In this simulation it was assumed that the respiration rate was decreasing linearly. Normally distributed noise was added to the calculated value of the DO.

Figure 5A:
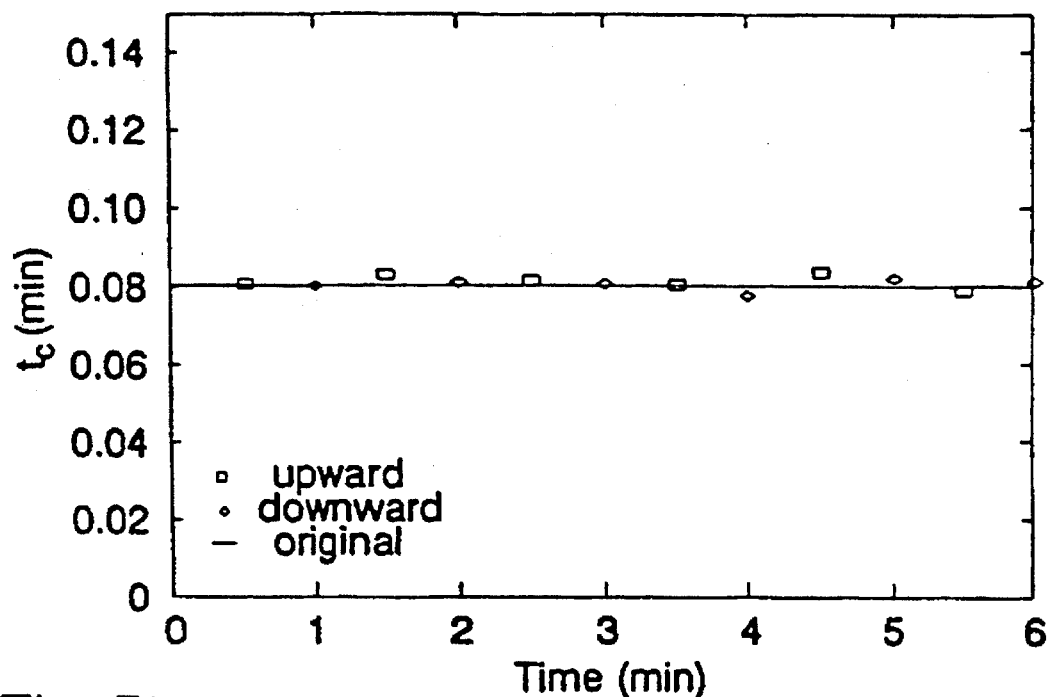
FIG. 5: Result of the estimation method applied on the simulated DO probe values (FIG. 4). Calculated values (points) compared with originally simulated values (solid lines). a. Probe response time constant ($t_c$). b. Real DO concentration (c).
Figure 5B:
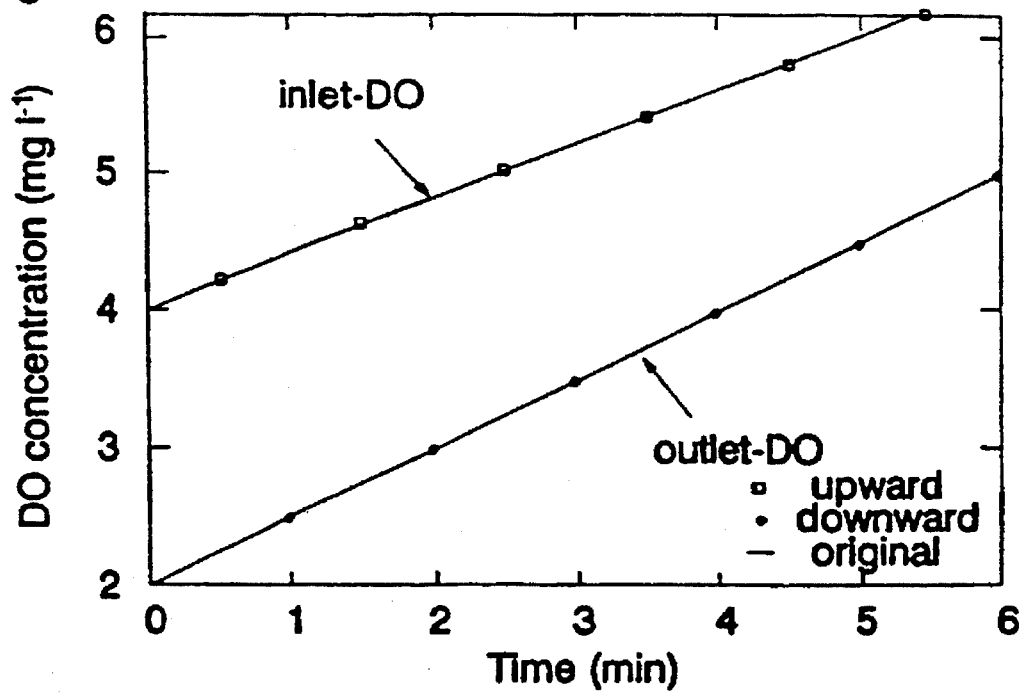

The simulated DO values were used to estimate $t_c$ and c employing the equations (7) through (13). FIG. 5 shows the result.

In case of an optimal estimation procedure, the resulting $t_c$ and c would have been the original points. The figure shows that $t_c$ (mean value 0.079±0.002 min) and c are estimated well.

Test 2: Non-linear change of the real DO concentration (simulation)

A batch experiment with the continuous flow-through respiration meter was simulated to test the assumption that, within the response measuring period, the change of the real DO concentration can be accurately represented by a linear relationship. In this experiment an amount of ammonium was added to the aerator connected to the respiration meter. The simulation model included Monod kinetics and a set of dynamic mass balances on DO and substrate for the aerator and the respiration chamber. The parameters were chosen from a fit of the simulation model on the experimental results of Spanjars and Klapwijk (1990 loc.cit.). In this test, unlike test 1, the change of the simulated DO is not linear any longer. Even so, in the calculation of $t_c$ and c, it is assumed to be linear within the response measuring interval.

Figure 6:
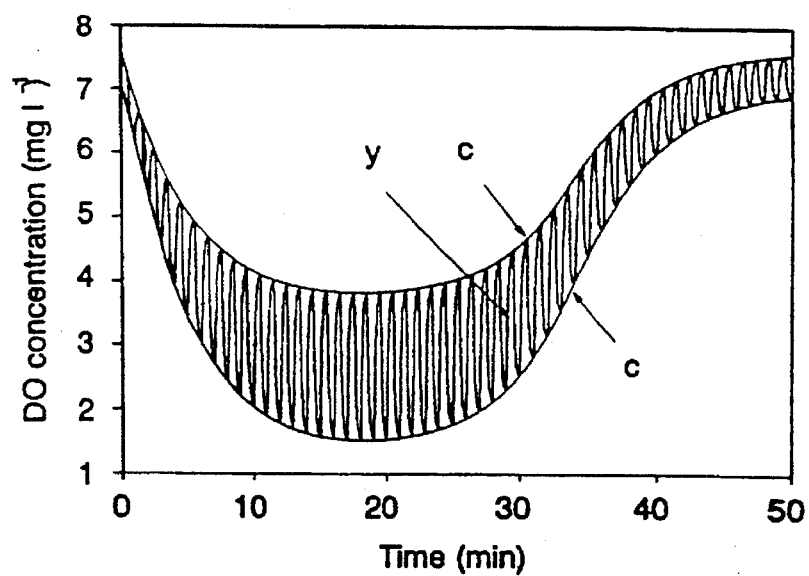
FIG. 6: Simulation of a batch experiment. Addition of 0.010 g ammonium-nitrogen to 1.5 liter sludge. Monod constants: $K=1.5$ g ammonium-nitrogen per m$^3$, maximum respiration rate=65 g m$^{-3}$ h$^{-1}$; Probe response time constant ($t_c$): 0.1 min; standard deviation noise: 0.01 g O$_2$ m$^{-3}$; Response measuring period ($t_r$): 30 s.

FIG. 6 shows the simulated DO concentration at the inlet and at the outlet of the respiration chamber as well as the simulated response of the DO probe.

Figure 7A:
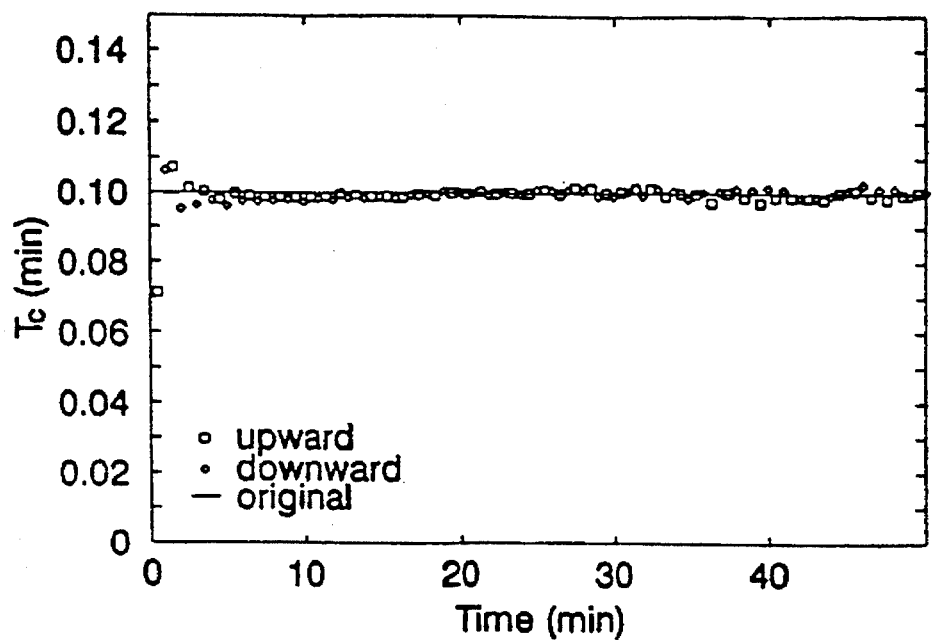
FIG. 7: Result of the estimation method for c and $t_c$ applied on the simulated DO probe values (FIG. 6). Estimated values (points) compared with the originally simulated values (solid lines). a: Probe response time constant ($t_c$). b. Real DO concentration (c).
Figure 7B:
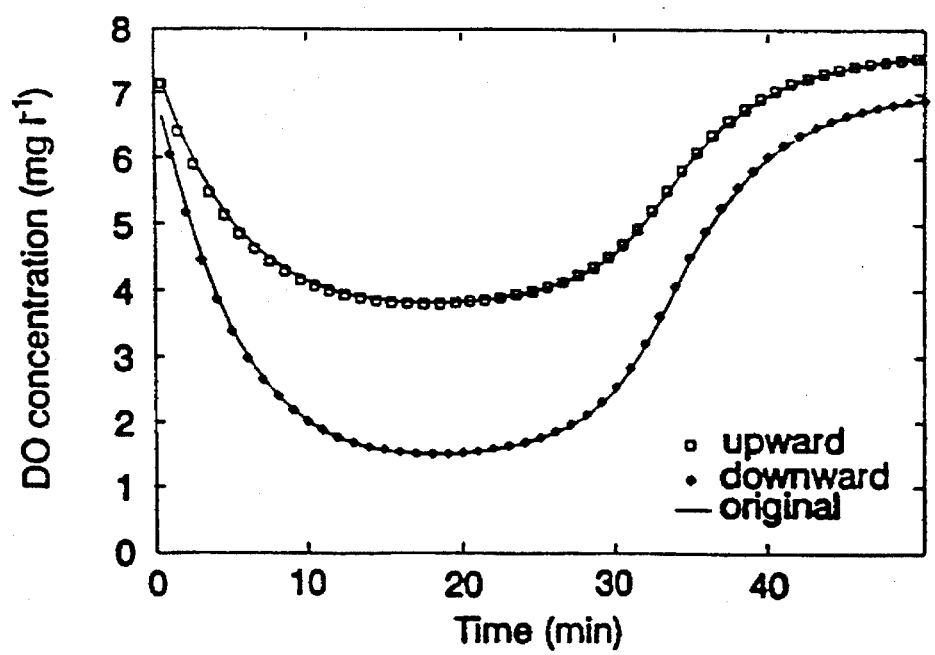

The simulated DO probe measurement values were used to estimate $t_c$ and c with the equations (9) through (13). FIG. 7 shows the result.

As in test 1, $t_c$ and c are estimated well (FIG. 7). $t_c$ does not depend on the magnitude of the response. The estimated DO is very close to the originally simulated DO.

From the results of test 1 and 2 it is concluded that the method proposed here allows the estimation of the first order response time constant and the real DO concentration.

Test 3: Experimental verification of the first order model

Figure 8A:
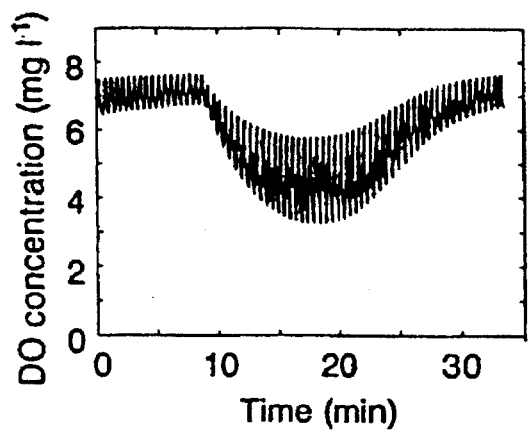
FIG. 8: DO-probe signal in a batch experiment: addition of 5 mg N as ammonium to activated sludge. a: full experiment; b: first 1.5 minutes of the experiment.
Figure 8B:
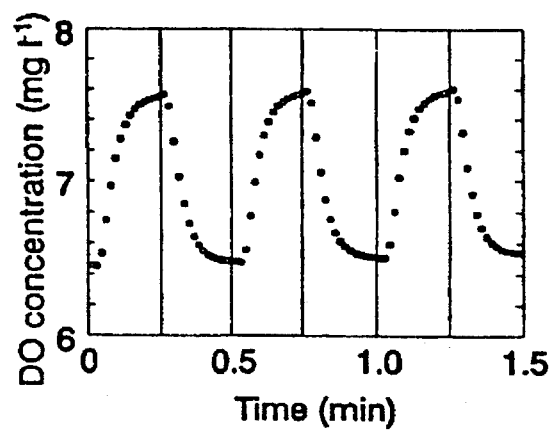

To test the assumption of the first order model, the experiment described and simulated in test 2 was carried out in the laboratory. In three experimental runs, the response measuring period (twice 15 s and once 20 s) was too short to attain the steady state response. Therefore this experiment was well suited to demonstrate the capability of the method to estimate the real DO concentration in the inlet and in the outlet of the respiration chamber. FIG. 8 shows the DO-probe signal.

Figure 9A:
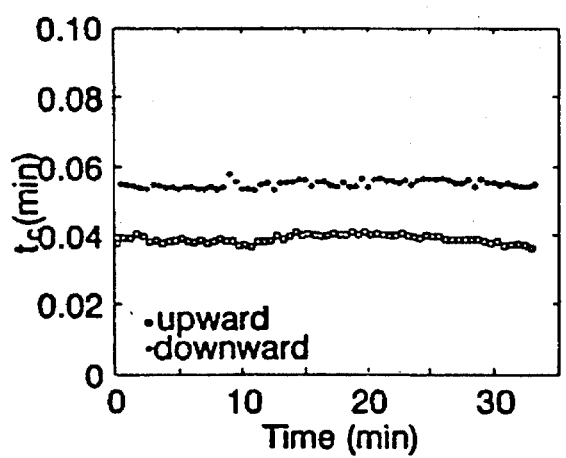
FIG. 9: $t_c$ calculated from the DO-probe measurement. a: without correction for dead time; b: with correction for dead time.

FIG. 9a shows the estimated $t_c$ for both the upward and the downward response. $t_c$ from the upward response is higher than $t_c$ from the downward response. Apparently, the model applied is not completely valid for both the upward and the downward response or both. After careful examination of the shape of the response curves (FIG. 8b) in relation to the geometry of the respiration meter (there was a dead space in one flow direction) it was concluded that a dead time ($t_d$) had to be incorporated in the model (3):

$$t_c \frac{dy}{dt} = -y + \alpha_0 + \alpha_1(t - t_d) \qquad (14)$$

Figure 9B:
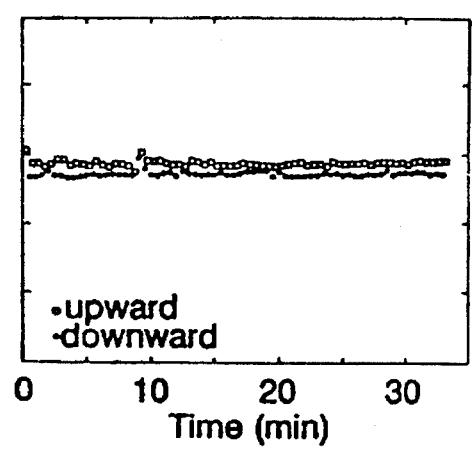

$t_d$ depends on the flow direction. In the experiments reported here, the values were found by trial and error to be 2 s and 1 s for the measurement of the inlet DO concentration and the outlet DO concentration respectively. FIG. 9b shows that when the dead time is accounted for, both responses produce almost similar $t_c$'s which also show less variation. As in test 2, $t_c$ is independent of the response amplitude.

Figure 10:
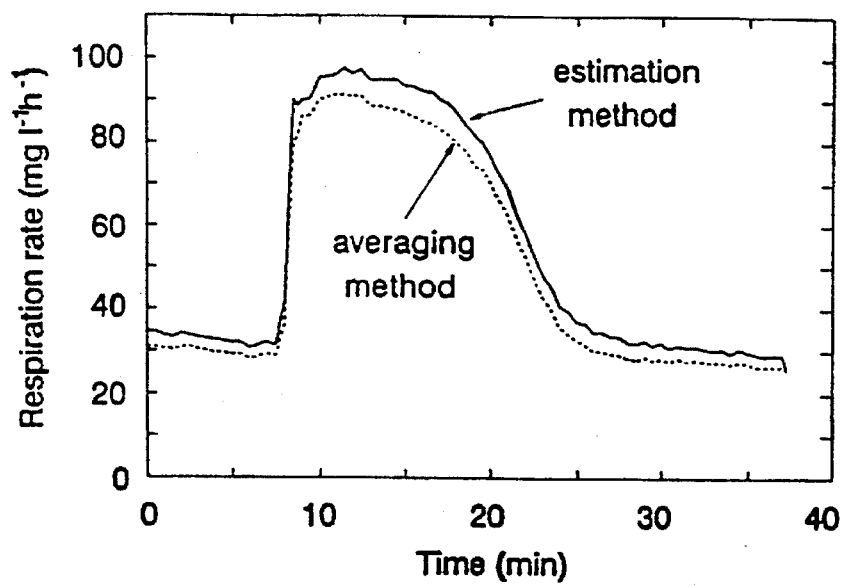
FIG. 10: Respiration rate calculated from the DO probe signal in FIG. 8. Comparison of the averaging method and the estimation method according to the invention.

The DO concentration at the inlet and at the outlet of the respiration chamber were calculated by averaging three measurements at the end of each response (averaging method) and by the method according to the invention. Next, the respiration rate was calculated as described by Spanjers and Klapwijk (1990 loc.cit.). The result is shown in FIG. 10.

The method according to the invention results in higher values for the respiration Pate, especially at a higher rate when the difference between inlet and outlet DO concentration is greater. It is difficult to verify the correctness of the absolute value of the respiration rate. Therefore, from the respiration rate, the total amount of oxygen additionally used to the endogenous oxygen consumption, defined as Short Term BOD ($BOD_{ST}$), was evaluated for both results. The $BOD_{ST}$ was calculated from the area under the respiration curves. This value divided by the amount of nitrogen added represents the mass of oxygen used by the nitrifiers for the oxidation of one unit of mass nitrogen (O/N ratio). Table 1 summarizes the results for the same experiment repeated with different response measuring periods.

TABLE 1

Comparison of the average method (average of three measurements at the end of the response measuring period) and the method according to the invention for different response measuring periods ($t_r$). Theoretical value O/N: 4.57; expected value 4.4.

| h (s) | $t_r$ (s) | O/N averaging method | method according to the invention | reference |
|---|---|---|---|---|
| 1 | 15 | 3.91 | 4.26 | this investigation |
| 1 | 15 | 3.74 | 4.01 | this investigation |
| 2 | 20 | 4.29 | 4.39 | this investigation |
| 2 | 30 | 4.02 | 4.04 | this investigation |
| 2 | 30 | 4.33 | 4.38 | this investigation |
| — | 30 | 4.36 | — | Spanjers and Klapwijk, 1990 loc.cit. |
| — | — | — | 4.33 | Sharma and Ahlert, 1977* |

*Sharma B. and Ahlert R.C. (1977), Nitrification and nitrogen removal. Wat. Res. 11, pp. 897–925

From table 1 two conclusions can be drawn.

Firstly, for a short response measuring period, the averaging method yields lower values for the O/N ratio while the estimation method according to the invention produces equal values compared to a large response measuring period. This means that the estimation method produces a better estimate of the real DO concentration. Two experiments yield a low O/N value from the estimation method compared to the value in the literature.

Secondly, the negligible difference between the two methods at a response measuring period of 30 s indicates that the effect of a changing real DO concentration on the probe response is marginal. For, in the determination of the O/N ratio there is a sharp change of the DO at only two different occasions. Another reason for the small difference is that the shift in both the endogenous as well as in the maximum respiration rate reduces the impact on the total amount of oxygen calculated from the area under the curve. Nevertheless, in kinetic experiments, when transients in the respiration rate and thus in DO concentration become important [Ossenbruggen P. et al., (1991) Designing experiments for model identification of the nitrification process; Watermatex 1991], the effect of the changing real DO will become stronger in the probe response.

From test 3 it is concluded that, for incomplete responses, the method according to the invention produces a better estimate of the real DO concentration and consequently a better result for the calculated respiration rate. Because of the actual geometry of the respiration meter, a correction in the response model for dead time is required.

EXAMPLE 2

Detection of probe fouling using the probe time constant.

In batch experiments is was attempted to detect probe failure from the estimated $t_c$. Therefore, the probe membrane was contaminated intentionally by covering part of the membrane with a thin layer of grease (approximately 10–25% of the surface).

First it was established that the contact of approximately the same amount of grease with the sludge in the aerator had no impact on either the DO concentration or the respiration rate. This means that the substance is not biodegradable or toxic on a short term and that it should neither provoke a change in the respiration rate when it is applied to the membrane surface.

Figure 11A:
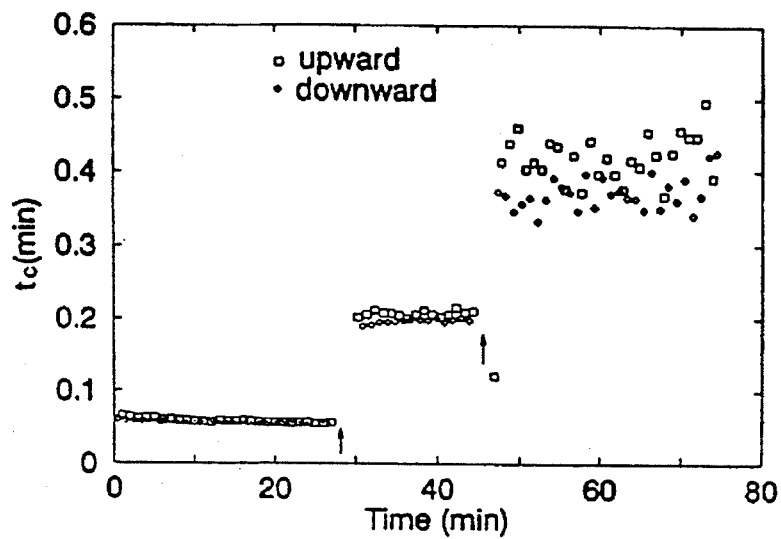
FIG. 11: Effect of the contamination of the probe membrane. a: Probe response time constant ($t_c$). b: Respiration rate; comparison of the averaging method and the estimation method according to the invention. c: Part of the DO probe signal (points) before and after contamination (respectively left and right), in comparison with the estimated DO.
Figure 11B:
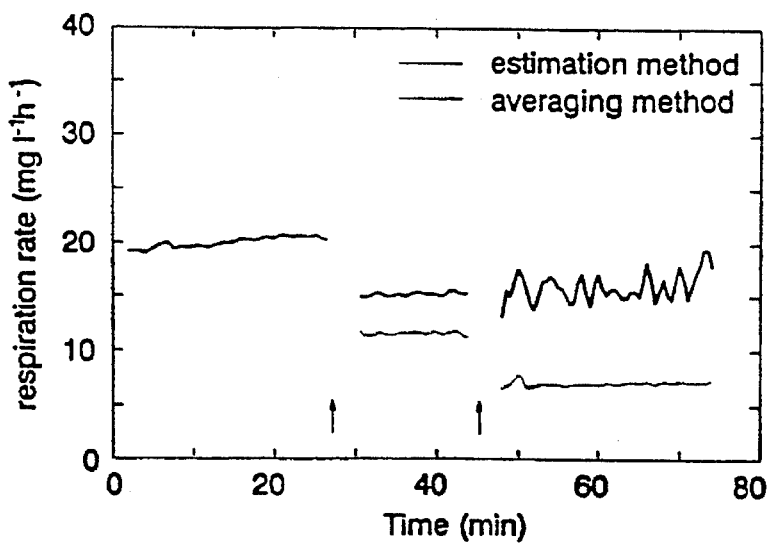

Two experiments were carried out. In the first experiment an amount of grease was applied twice to the membrane, while the respiration meter was measuring the endogenous respiration rate. In FIG. 11a the estimated $t_c$ is shown and the applications of grease are indicated. The figure shows that a greater amount of grease results in an increasing $t_c$ meaning that the probe becomes slower. Consequently, the DO concentration calculated from the end values of the response measuring period (averaging method) is erroneous and so is the calculated respiration rate (FIG. 11b). The DO from the method according to the invention and so the calculated respiration rate is affected to a lesser extent by the deterioration of the probe: after the first treatment the rate decreases from 20 to 15 gm$^{-3}$ h$^{-1}$; after the second treatment it remains on this level, although the noise has increased. This decrease may partly be caused by another incident, for example the real endogenous respiration rate may have decreased during the time that the membrane was being contaminated. This is supported by the check at the end of the experiment where the membrane was replaced by a new one and the respiration rate was found to be 18 mg l$^{-1}$ h$^{-1}$.

Figure 11C:
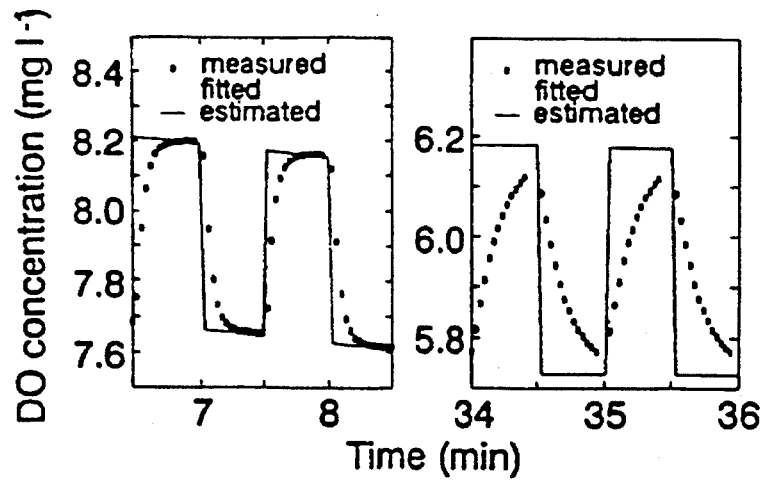

FIG. 11c illustrates the effect of the contamination on the individual response curves. In this figure the estimated DO according to the invention is also indicated.

Figure 12A:
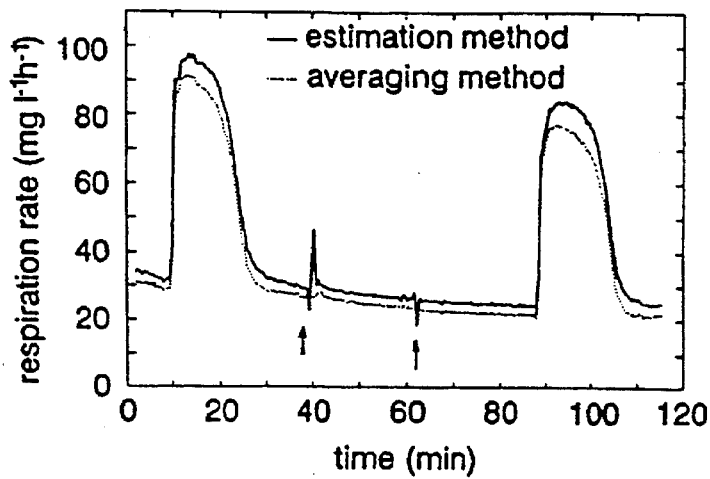
FIG. 12: Addition of 0.005 g N (as ammonium) to 1.5 l of activated sludge, before and after contamination of the probe membrane. a: Respiration rate calculated from the DO concentration. Comparison of the averaging method and the method according to the invention. b: Probe response time constant ($t_c$).
Figure 12B:
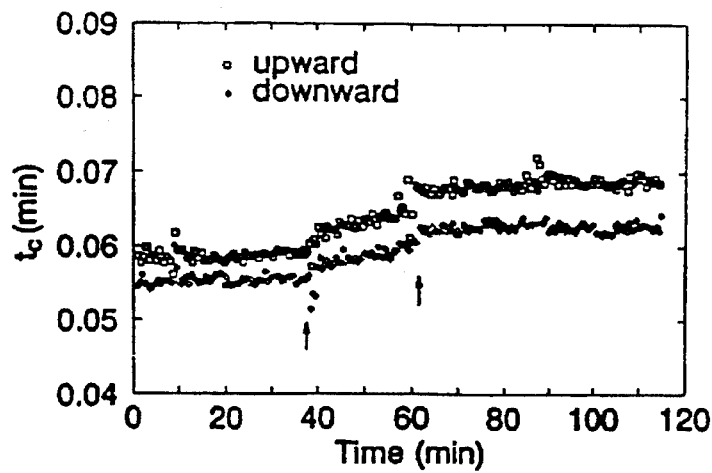

In the second experiment ammonium was added twice to activated sludge in the endogenous phase of respiration. The first addition is already reported in the previous section (FIG. 10 and table 1). The second addition was done after contamination of the membrane, FIG. 12a shows the respiration rate calculated from the DO concentration, whereas $t_c$ is plotted in FIG. 12b. The O/N ratio was calculated from the respiration rate (table 2).

TABLE 2

Effect of the contamination of the probe membrane on the calculated O/N value. Comparison of the averaging method (averaging three measurements at the end of the response measuring period) and the method according to the invention. h = 1 s, $t_r$ = 15 s, theoretical O/N ratio: 4.57.

| | O/N | |
|---|---|---|
| | averaging method | method according to the invention |
| before contamination | 3.91 | 4.26 |
| after contamination | 3.04 | 4.28 |

From table 2 it can be concluded that the O/N ratio evaluated from the method according to the invention is not affected by the probe deterioration while the O/N ratio from the averaging method (already lower because of the short response measuring period, see table 1) is decreased.

CONCLUSION

As indicated above the purpose of the investigation of Applicant was to develop a method to detect the need for calibrating a probe and to improve the measurement of substances with probes which deliver an electric signal such as DO-probes. In the investigation a respiration meter was used with one and the same DO-probe at the inlet and at the outlet of a respiration chamber. Inherent in the principle of the respiration meter is that the DO-probe is repeatedly subjected to step changes in the DO concentration. This fact is employed, for the improvement of the DO measurement, by fitting a first order response model to each measured response, which provides an estimation of the real DO concentration and of the first order probe response time constant. The change of the real DO concentration during the response measurement is accounted for in the model.

The simulations show that the method allows the calculation of c and $t_c$. On the condition that the probe signal can be modelled by a first order dynamic system, a correct estimation of c and $t_c$ can be obtained from experimental data. The type of the response is chiefly determined by the manufacturer of the DO meter. However the response is also partly determined by conditions of the respiration meter in which the probe is mounted. The experiments show that, in this case, the assumption of a first order response is reasonable, provided a dead time is accounted for. This dead time is fixed by the respiration meter and can be determined exactly by measuring the dead space. The experiments also show that it is reasonable to assume that the change of the real DO concentration within one response measuring period can be approximated by a linear relationship. This can be clearly illustrated by looking at an enlarged portion of FIG. 8a.

The DO concentration c can be estimated from only a part of the probe response, where the signal has not yet reached its steady state. The advantage, in the respiration measurement, is that the measuring frequency of the DO's at the inlet and at the outlet and herewith the measuring frequency of the respiration rate can be increased.

$t_c$ indicates malfunction of the probe even in case of severe deterioration (FIG. 11a), when the probe becomes very slow and the estimation of c likely becomes unreliable.

The method according to the invention, for the estimation of $t_c$ and c, can also be used, in combination with the measuring technique, in the measurement of the DO concentration in an activated sludge reactor. On the condition that the respiration meter is installed close to the reactor, the DO concentration in the inflow of the respiration meter is equal to the concentration in the reactor at the sampling point [Kim C. W. et al, (1991), Continuous determination of oxygen transfer coefficient with an on-line respiration meter. Proceedings: 3rd IAWPRC regional conference on development and water pollution control, November 20–24, Shanghai]. Besides the measurement of the DO concentration and the optional measurement of the respiration rate this technique, through the estimated $t_c$, provides a continuous diagnosis of the probe condition.

As appears from the Examples reported above, the method according to the invention provides a reliable estimate of the real DO concentration from the probe response signal when the probe is subjected, in the respiration measurement, to a repeated, stepwise changing DO concentration. As a result, the reliability of the calculated respiration rate is improved.

The first order probe response constant $t_c$, evaluated from the probe signal is a useful indicator for detecting fouling of the probe membrane.

I claim:

1. Method for detecting the need for calibrating a probe, which probe delivers an electric signal on account of a change of the concentration of a substance to be measured, comprising:

(a) subjecting the probe to consecutive changes of the concentration of the substance to be measured by providing the probe alternately with at least two different concentrations;

(b) calculating the value of the probe response time constant $t_c$, the constants $\alpha_0$ and $\alpha_1$ of a probe response curve after the instant change of the concentration with the following main equation:

$$t_c \frac{dy}{dt} = -y + \alpha_0 + \alpha_1 t$$

wherein t=time (time)

$t_c$=probe response time constant (time)

y=substance probe signal (mass volume$^{-1}$)

$\alpha_0$=substance concentration at start of response (mass volume$^{-1}$)

$\alpha_1$=rate of change of substance concentration (mass volume$^{-1}$ time$^{-1}$) and (c) comparing the calculated $t_c$-values of at least two different measurements with each other and—in case the calculated $t_c$-values do not match—calibrating the probe.

2. Method according to claim 1, wherein the probe is a dissolved oxygen (DO) measuring probe.

3. Method according to claim 2, wherein the consecutive changes of the DO concentration is carried out by providing the DO measuring probe alternately with at least two flows having a different DO concentration.

4. Method according to claim 2, wherein the consecutive changes of the DO concentration is carried out by alternately reversing the flow direction of a reacting DO containing medium, flowing through a closed chamber provided with one single probe at only one opening of said chamber.

5. Method according to claim 4, wherein the DO containing medium is activated sludge.

6. Method for calculating the real value of a probe, which probe delivers an electric signal on account of a change of the concentration of a substance to be measured, comprising:

(a) subjecting the probe to consecutive changes of the concentration of the substance to be measured by providing the probe alternately with at least two different concentrations;

(b) calculating the real value of the probe which is equal to $\alpha_0 + \alpha_1 t$ of a probe response curve after the instant change of the concentration with following main equation:

$$t_c \frac{dy}{dt} = -y + \alpha_0 + \alpha_1 t$$

wherein $t$ = time (time)

$t_c$ = probe response time constant (time)

$y$ = substance probe signal (mass volume$^{-1}$)

$\alpha_0$ = substance concentration at start of response (mass volume$^{-1}$)

$\alpha_1$ = rate of change of substance concentration (mass volume$^{-1}$ time$^{-1}$).

* * * * *